(12) United States Patent
Thomas (10) Patent No.: US 9,498,322 B2
(45) Date of Patent: Nov. 22, 2016

(54) MULTI-PORTION ENDOLUMINAL PROSTHESIS

(75) Inventor: Barry A. Thomas, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 598 days.

(21) Appl. No.: 11/541,021

(22) Filed: Sep. 29, 2006

(65) Prior Publication Data

US 2008/0082157 A1    Apr. 3, 2008

Related U.S. Application Data

(63) Continuation of application No. PCT/US2005/006995, filed on Mar. 1, 2005.

(60) Provisional application No. 60/558,295, filed on Mar. 31, 2004.

(51) Int. Cl.
| | | |
|---|---|---|
| *A61F 2/06* | (2013.01) | |
| *A61F 2/07* | (2013.01) | |
| *A61F 2/95* | (2013.01) | |
| *A61F 2/89* | (2013.01) | |

(52) U.S. Cl.
CPC .. *A61F 2/07* (2013.01); *A61F 2/89* (2013.01); *A61F 2/95* (2013.01); *A61F 2002/075* (2013.01); *A61F 2002/9511* (2013.01); *A61F 2250/0031* (2013.01)

(58) Field of Classification Search
CPC .... A61F 2/07; A61F 2/89; A61F 2210/0004; A61F 2002/30034; A61F 2250/0031; A61L 31/148

USPC ........................................................ 623/1.13
See application file for complete search history.

(56) References Cited

U.S. PATENT DOCUMENTS

| | | |
|---|---|---|
| 4,562,596 A | 1/1986 | Kornberg |
| 4,665,918 A | 5/1987 | Garza et al. |
| 4,902,508 A | 2/1990 | Badylak et al. |
| 4,950,227 A | 8/1990 | Savin et al. |
| 5,059,211 A | 10/1991 | Stack et al. |
| 5,085,629 A | 2/1992 | Goldberg et al. |
| 5,306,286 A | 4/1994 | Stack et al. |
| 5,387,235 A | 2/1995 | Chuter |
| 5,443,458 A | 8/1995 | Eury |
| 5,464,450 A | 11/1995 | Buscemi et al. |

(Continued)

FOREIGN PATENT DOCUMENTS

| | | |
|---|---|---|
| GB | 2347861 | 9/2000 |
| WO | 9822158 | 5/1998 |

(Continued)

OTHER PUBLICATIONS

Jul. 27, 2005, Cook Inc.—Search Report PCT/US2005/006995.

(Continued)

*Primary Examiner* — Julie A Szpira
(74) *Attorney, Agent, or Firm* — Brinks Gilson & Lione (57) ABSTRACT

An endoluminal prosthesis for occluding a dissection of an aorta has a tube with a first portion and a second portion. The second portion of the tube comprises a bioaborbable material. The prosthesis also comprises a stent coupled to the tube. The prosthesis is configured for endoluminal placement in the aorta via an artery.

17 Claims, 11 Drawing Sheets

(56) References Cited

U.S. PATENT DOCUMENTS

| | | | |
|---|---|---|---|
| 5,500,013 | A | 3/1996 | Buscemi et al. |
| 5,551,954 | A | 9/1996 | Buscemi et al. |
| 5,629,077 | A | 5/1997 | Turnlund et al. |
| 5,670,161 | A | 9/1997 | Healy et al. |
| 5,711,969 | A | 1/1998 | Patel et al. |
| 5,720,776 | A | 2/1998 | Chuter et al. |
| 5,733,337 | A | 3/1998 | Carr, Jr. et al. |
| 5,766,710 | A | 6/1998 | Turnlund et al. |
| 5,769,883 | A | 6/1998 | Buscemi et al. |
| 5,792,106 | A | 8/1998 | Mische |
| 5,885,619 | A | 3/1999 | Patel et al. |
| 5,955,110 | A | 9/1999 | Patel et al. |
| 5,968,096 | A | 10/1999 | Whitson et al. |
| 6,206,931 | B1 | 3/2001 | Cook et al. |
| 6,673,102 | B1 | 1/2004 | Vonesh et al. |
| 2001/0041928 | A1* | 11/2001 | Pavcnik et al. ............ 623/1.13 |
| 2002/0052648 | A1* | 5/2002 | McGuckin et al. ......... 623/1.35 |
| 2002/0143384 | A1* | 10/2002 | Ozasa ......................... 623/1.12 |
| 2002/0165601 | A1* | 11/2002 | Clerc ........................... 623/1.13 |
| 2003/0130721 | A1* | 7/2003 | Martin et al. ............... 623/1.13 |
| 2003/0225446 | A1* | 12/2003 | Hartley ....................... 623/1.11 |
| 2003/0233140 | A1 | 12/2003 | Hartley et al. |
| 2004/0054396 | A1 | 3/2004 | Hartley et al. |
| 2004/0082989 | A1 | 4/2004 | Cook et al. ................. 623/1.13 |
| 2004/0098079 | A1 | 5/2004 | Hartley et al. |
| 2004/0176832 | A1* | 9/2004 | Hartley et al. .............. 623/1.11 |
| 2005/0220848 | A1* | 10/2005 | Bates ........................... 424/443 |
| 2005/0273155 | A1* | 12/2005 | Bahler et al. ............... 623/1.13 |
| 2008/0046063 | A1* | 2/2008 | Boatman et al. ........... 623/1.11 |

FOREIGN PATENT DOCUMENTS

| | | |
|---|---|---|
| WO | 9853761 A1 | 12/1998 |
| WO | 9929262 A1 | 6/1999 |
| WO | 03034948 A1 | 5/2003 |
| WO | 03053287 A1 | 7/2003 |
| WO | 2004016200 | 2/2004 |
| WO | WO 2004/017866 A1 | 3/2004 |
| WO | 2004049978 | 6/2004 |
| WO | WO 2005/102221 A1 | 11/2005 |

OTHER PUBLICATIONS

Jul. 27, 2005, Cook Inc.—Written Opinion PCT/US2005/006995.

T. Huynh, G. Abraham, J. Murray, K. Brockbank, P. Hagen, S. Sullivan, Remodeling of an Acellular Collagen Graft into a Physiologically Responsive Neovessel, Nature Biotechnology, Nov. 1, 1999, p. 1083-1086, vol. 17, Nature Publishing Group, U.S.

International Search Report for corresponding PCT/US2005/006995 dated Jul. 27, 2005 (3 pages).

* cited by examiner

MULTI-PORTION ENDOLUMINAL PROSTHESIS

The instant application is a Continuation of PCT/US2005/006995 filed on Mar. 1, 2005, which claims priority from Provisional Application No. 60/558,295, filed Mar. 31, 2004.

TECHNICAL FIELD

This invention relates to a medical device and, in particular, a prosthesis for implantation within the human or animal body for the repair of an aortic dissection or intramural hematoma, and a method for implanting the same.

BACKGROUND OF THE INVENTION

Throughout this specification, when discussing the aorta or other blood vessels, the terms distal and distally with respect to a prosthesis are intended to refer to the end of the prosthesis furthest away in the direction of blood flow from the heart. Similarly, the terms proximal and proximally are intended to mean the end of the prosthesis which, when implanted, would be nearest to the heart.

The aorta, as are all arteries, is made up of three layers. The inner layer of the aorta is known as the tunica intima, and comprises mainly endothelial cells. The middle layer of the aorta is called a tunica media, and consists of smooth muscle and elastic tissue. The outer layer of the aorta is referred to as the tunica adventitia, and is composed of connective tissue.

An aortic dissection is a tear or partial tear in the tunica intima, or lining, of the aorta. This tear results in a "flap" at the opening, which may occlude blood flow in the aorta. In an aortic dissection, blood penetrates the intima through the tear, and enters the media. The pressure of the blood rips the layers of the media apart, allowing more blood to enter. This process can propagate a tear along the length of the aorta for some distance, creating a blood filled channel known as a "false lumen". Over time, such a continuous flow of blood through a false lumen may cause the aorta to rupture, a serious condition often resulting in death.

There are two types of aortic dissections under the Stanford rating system. A dissection of the ascending aorta is classified as a Type A dissection. A dissection of the descending aorta is classified as a Type B dissection. Type A dissections can be treated medically, but usually only briefly. Type A dissections are usually treated with interventional catheterization or open surgical techniques. Type B dissections are most often treated medically with routine monitoring and prescribed medications. Type B dissections may also be treated surgically, but this option carries substantially increased risk of paralysis, and therefore is not commonly preformed.

The deployment of intraluminal prostheses into the lumen of a patient from a remote location by the use of a deployment device or introducer has been disclosed in a number of earlier patens and patent applications. U.S. Pat. No. 4,562,596 entitled "Aortic Graft, Device and Method for Performing an Intraluminal Abdominal Aortic Aneurysm Repair" proposes the retention of a self-expanding graft within a sleeve until it is to be deployed, at which time the sleeve is withdrawn and the graft is allowed to expand. These features and other features disclosed in U.S. Pat. No. 4,562,596 could be used with the present invention and the disclosure of the U.S. Pat. No. 4,562,596 is herein incorporated by reference.

U.S. Pat. No. 4,665,918 entitled "Prosthesis System and Method" proposes a system and method for the deployment of a prosthesis in a blood vessel. The prosthesis is positioned between a delivery catheter and an outer sheath and expands outwardly upon removal of the sheath. These features and other features disclosed in U.S. Pat. No. 4,665,918 could be used with the present invention and the disclosure of the U.S. Pat. No. 4,665,918 is herein incorporated by reference.

U.S. Pat. No. 4,950,227 entitled "Stent Delivery System" proposed the delivery of a stent by mounting the stent to the outside of an inflatable catheter and retaining the ends of an unexpanded stent by fitting a sleeve over either end of the stent. Expansion of the stent is caused by inflation of the catheter between the sleeves so that the ends of the stent are withdrawn from the respective sleeves and the stend released and expanded into position. These features and other features disclosed in U.S. Pat. No. 4,950,227 could be used with the present invention and the disclosure of the U.S. Pat. No. 4,950,227 is herein incorporated by reference.

U.S. Pat. No. 5,387,235 entitled "Endovascular Transluminal Graft Prosthesis for Repair of Aneurysm" discloses apparatus and methods fo retaining grafts onto deployment devices. These features and other features disclosed in U.S. Pat. No. 5,387,235 could be used with the present invention and the disclosure of the U.S. Pat. No. 5,387,235 is herein incorporated by reference.

U.S. Pat. No. 5,720,776 entitled "Barb and Expandable Transluminal Graft Prosthesis for Repair of Aneurysm" disclosed improved barbs with various forms of mechanical attachment to a stent. These features and other features disclosed in U.S. Pat. No. 5,720,776 could be used with the present invention and the disclosure of the U.S. Pat. No. 5,720,776 is herein incorporated by reference.

U.S. Pat. No. 6,206,931 entitled "Graft Prosthesis Materials" discloses graft prosthesis material and a method for implanting, transplanting, replacing and repairing a part of a patient and particularly the manufacture and use of a purified, collagen based matrix structure removed from a submucosa tissue source. These features and other features disclosed in U.S. Pat. No. 6,206,931 could be used with the present invention and the disclosure of the U.S. Pat. No. 6,206,931 is herein incorporated by reference.

PCT Patent Publication Number No. WO99/29262 entitled "Endoluminal Aortic Stents" discloses a fenestrated prosthesis for placement where there are intersecting arteries. This feature and other features disclosed in PCT Patent Publication Number No. WO99/29262 could be used with the present invention and the disclosure of PCT Patent Publication Number No. WO99/29262 is herein incorporated by reference.

PCT Patent Publication Number No. WO03/034948 entitled "Prostheses for Curved Lumens" discloses prostheses with arrangements for bending the prosthesis for placement into curved lumens. This feature and other features disclosed in PCT Patent Publication Number No. WO03/034948 could be used with the present invention and the disclosure of PCT Patent Publication Number No. WO03/034948 is herein incorporated by reference.

United States Patent Application Publication No. 2003/0233140 entitled "Trigger Wire System" discloses release wire systems for the release of stent grafts retained on introducer devices. This feature and other features disclosed in United States Patent Application Publication No. 2003/0233140 could be used with the present invention and the disclosure United States Patent Application Publication No. 2003/0233140 is herein incorporated by reference.

United States Patent Application Publication No. 2004/0098079 entitled "Thoracic Aortic Stent Graft Deployment Device" discloses introducer devices adapted for deployment of stent grafts particularly in the thoracic arch. This feature and other features disclosed in United States Patent Application Publication No. 2004/0098079 could be used with the present invention and the disclosure United States Patent Application Publication No. 2004/0098079 is herein incorporated by reference.

United States Patent Application Publication No. 2004/0054396 entitled "Stent-Graft Fastening" discloses arrangements for fastening stents onto grafts particularly exposed stents. This feature and other features disclosed in United States Patent Application Publication No. 2004/0054396 could be used with the present invention and the disclosure United States Patent Application Publication No. 2004/0054396 is herein incorporated by reference.

PCT Patent Publication Number No. WO03/053287 entitled "Stent Graft with Improved Graft Adhesion" discloses arrangements on stent grafts for enhancing the adhesion of such stent grafts into walls of vessels in which they are deployed. This feature and other features disclosed in PCT Patent Publication Number No. WO03/053287 could be used with the present invention and the disclosure of PCT Patent Publication Number No. WO03/053287 is herein incorporated by reference.

PCT Patent Publication Number No. WO98/53761 entitled "A Prosthesis and a Method and Means of Deploying a Prosthesis", which is herein incorporated by reference, discloses various embodiments fo an introducer for positioning an expandable endovascular prosthesis in a lumen of a patient that could be used with the present invention.

SUMMARY OF THE INVENTION

An endoluminal prosthesis for occluding a dissection of an aorta has a tube with a first portion and a second portion. The second portion of the tube comprises a bioasborbable material. The prosthesis also comprises a stent coupled to the tube. The prosthesis is configured for endoluminal placement in the aorta via an artery.

The first portion of the tube can comprise a non-porous material, such as a derived collagen or a synthetic material. The derived collagen material can be an extracellular collagen matrix, such as small intestinal submucosa, pericardium, liver basement membrane, or the like. The synthetic material can be polyester, polytetrafluoroethylene, or the like. The second portion of the tube can comprise a polyglactin, polyglycolic acid, ployglyconate, polydioxanone, or another bioabsorbable material.

Then endoluminal prosthesis can be placed in a dissected aorta so that the second portion of the tube is adjacent to the dissection. The bioabsorbable material can be a surgical mesh or a surgical knit, that, when held adjacent to the dissection, facilitates healing of the dissection. In time, after the dissection has healed, this bioabsorbable material is absorbed. The first portion of the tube, however, remains in place to provide continued reinforcement for the aorta.

The invention can be better understood with reference to the following drawings and descriptions. The components in the figures are not necessarily to scale, emphasis instead being placed upon illustrating the principles of the invention. Moreover, in the figures, like reference numerals designate corresponding parts throughout the different views.

DETAILED DESCRIPTION

Figure 1:
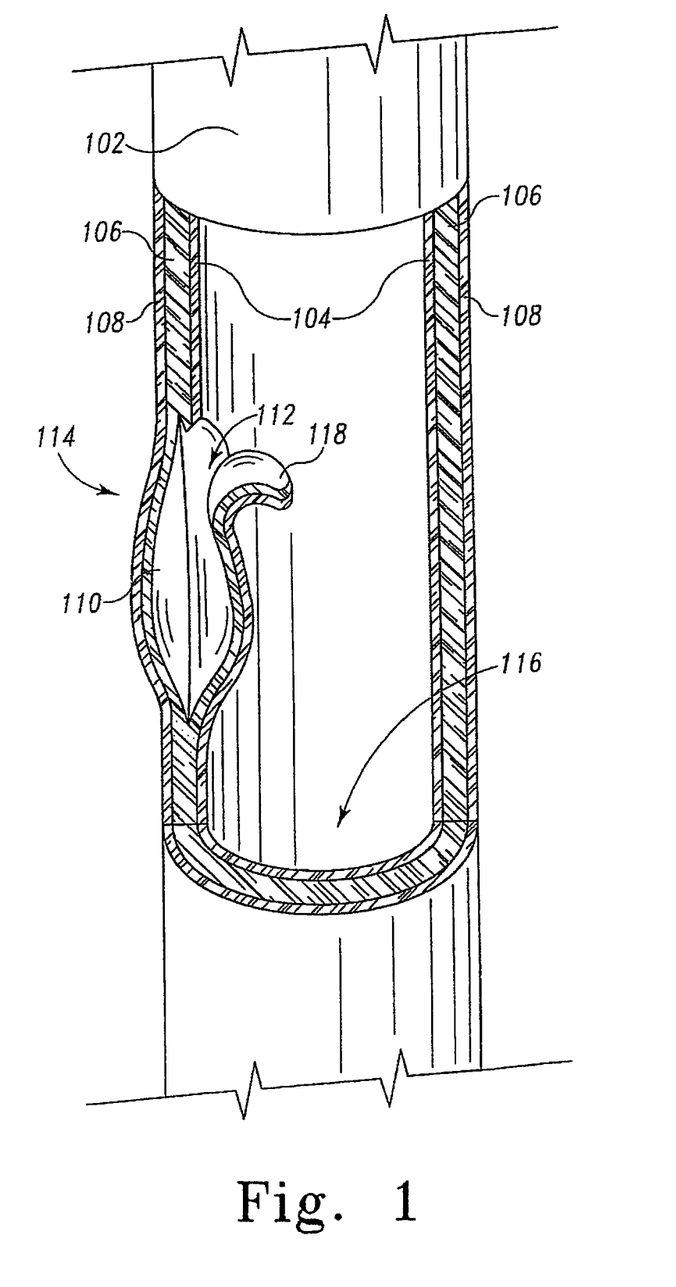
FIG. 1 is a partial cut-away view of an aorta.

FIG. 1 is a partial cut-away view of an aorta 102, including three layers of the aorta: an intima 104, a media 106 and an adventitia 108. The aorta 102 is dissected so that a flap 118 exposes an opening 112 to a false lumen 110. An aneurysm 114 has developed at the site of the false lumen 110, which may cause increased stress on the adventitia 108.

The dissected aorta 102 presents two conditions that should be treated. First, the aneurysm 114 may continue to develop, eventually causing the adventitia 108 to rupture. Such a rupture may allow blood to flow from the false lumen 110 into tissue (not shown) surrounding the aorta 102. Second, the flap 118 may obstruct blood flow in a true lumen 116 of the aorta. An obstruction of the true lumen 116 may cause decreased profusion distally from the flap 118.

Figure 2:
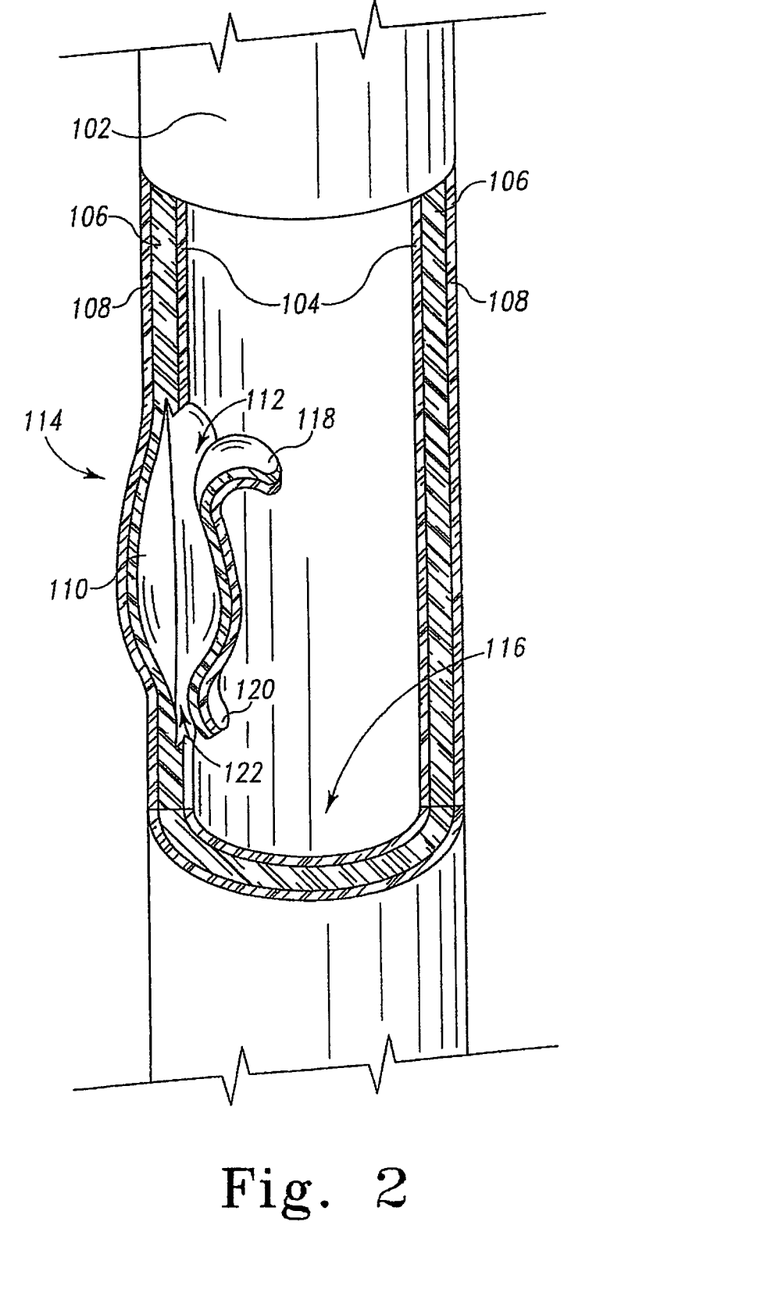
FIG. 2 is a partial cut-away view of the aorta of FIG. 1.

FIG. 2 is another partial cut-away view of the aorta 102 wherein the false lumen 110 has propagated to a second opening 122, which exits the lumen through a second flap 120 torn in the intima 104. In this case, the false lumen 110 may expand radially so as to become as large as or larger than the true lumen 116. Besides increasing the risk that the aneurysm 114 will rupture, such an expansion of the false lumen 110 may decrease the profusion to branch vessels (not shown) that are profused by the true lumen 116.

Figure 3:
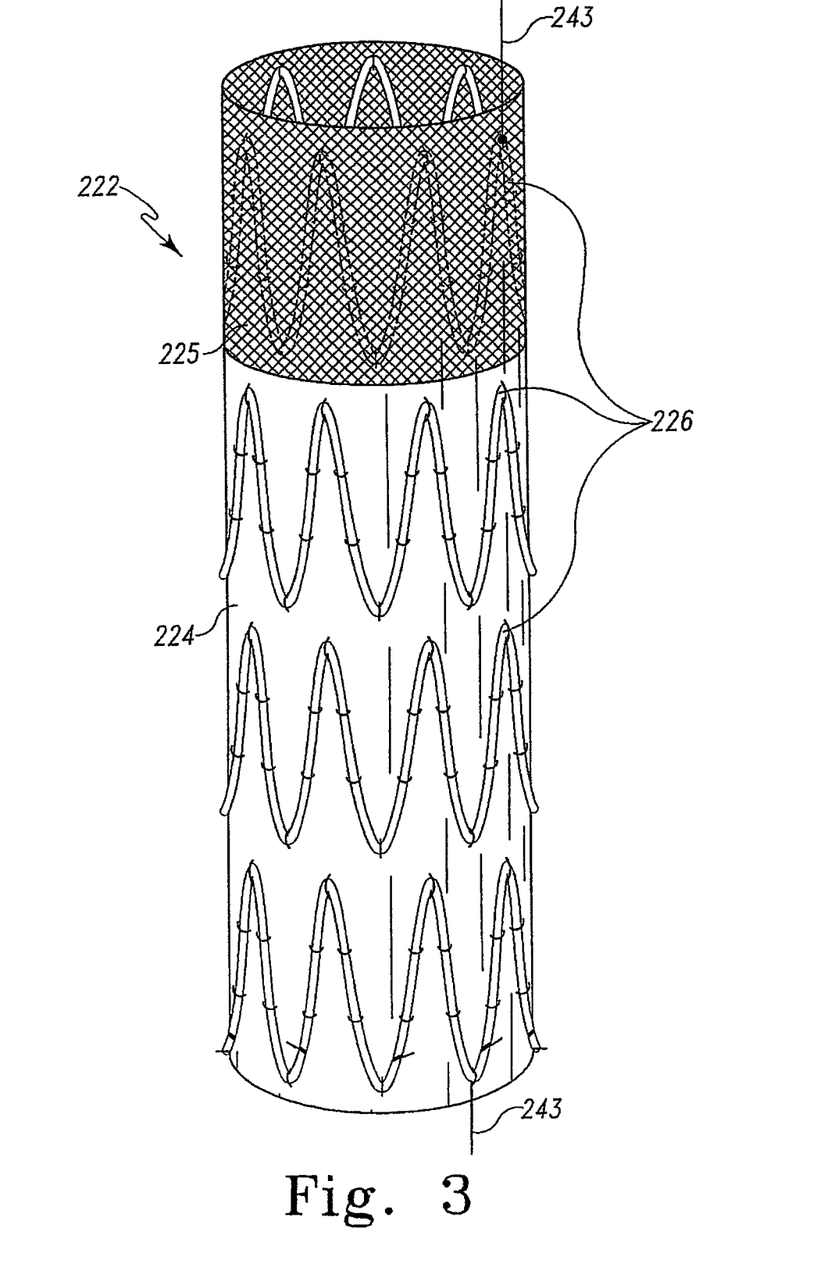
FIG. 3 is a perspective view of an endoluminal prosthesis.
Figure 3A:
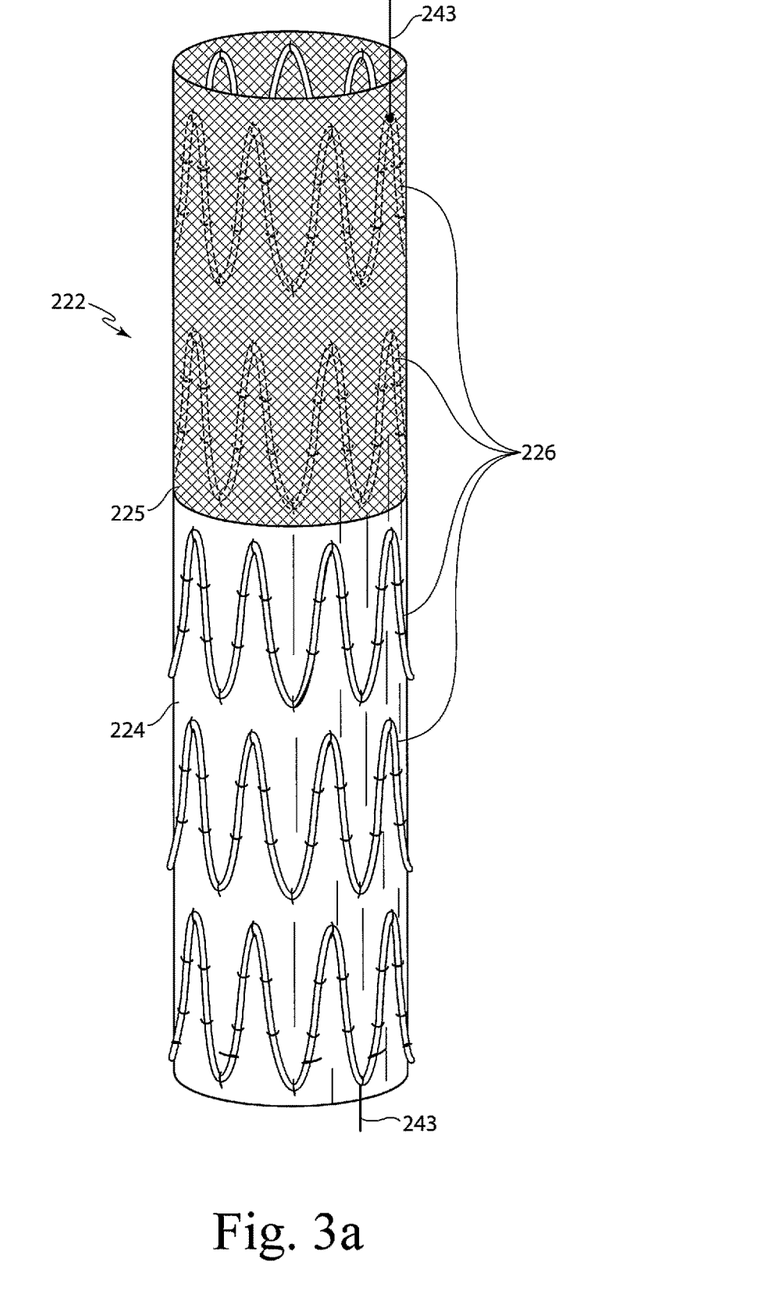
FIG. 3A is a perspective view of another endoluminal prosthesis.

FIGS. 3 and 3a are perspective views of endoluminal prostheses 222. The term "prosthesis" means any replacement for a body part or function of that body part. The term "prosthesis" can also mean a device that enhances or adds functionality to a physiological system. The terms "endoluminal" and "intraluminal" describe objects that are found or can be placed inside a lumen in the human or animal body. A lumen can be an existing lumen or a lumen created by surgical intervention. This includes lumens such as blood vessels, parts of the gastrointestinal tract, ducts such as bile ducts, parts of the respiratory system, etc. "Endoluminal prosthesis" thus describes a prosthesis that can be placed inside one of these lumens.

The prosthesis 222 comprises a first tubular graft material 224 and a second tubular graft material 225, each of which can have one or more self-expanding stents 226 attached thereto. Alternatively, the first tubular graft material 224 and a second tubular graft material 225 can have balloon expandable stents (not shown) instead of or in addition to the one or more self-expanding stents 226.

The term "graft" means the generally cannular of tubular member which acts as an artificial vessel. A graft by itself or with the addition of other elements can be an endoluminal prosthesis. The term "stent" means any device or structure that adds rigidity, expansion force or support to a prosthesis. Stents useful in the present invention can be metallic or bioabsorbable. Bioabsorbable stents can be made from polyhydroxyalkanoate, poly(alpha-hydroxy acid) such as polylactide [poly-L-lactide (PLLA), poly-D-lactide (PDLA)], polyglycolide (PGA), polydioxanone, polycaprolactone, polygluconate, polylactic acid-polyethylene oxide copolymers, poly(hydroxybutyrate), polyanhydride, polyphophoester, poly(amino acids), or related copolymers materials, each of which have a characteristic degradation rate in the body. For example, PGA and polydioxanone are relatively fast-bioabsorbing materials (weeks to months) and PLA and polycaprolactone are relatively slo-bioabsorbing material (months to years). Bioabsorbable stents can be fabricated according to the methods and procedures described, for example, in U.S. Pat. Nos. 5,792,106; 5,769,883; 5,766,710; 5,670,161; 5,629,077; 5,551,954; 5,500,013; 5,464,450; 5,443,458; 5,306,286; 5,059,211, and 5,085,629.

The first tubular graft material 224 is preferably nonporous so that it does not leak or sweat under physiological forces. The graft material is preferably woven DACRON® polyester (VASCUTEK®) Ltd, Renfrewshire, Scotland, UK). The first tubular graft material 224 can be made of any other at least substantially biocompatible material including such materials as other polyester fabrics, polytetrafluroroethylene (PTFE), expanded PTFE, and other synthetic materials. Naturally occurring biomaterials, such as collagen, are also highly desirable, particularly a derived collagen material know as extracellular collagen matrix (ECM), such as small intestinal submucosa (SIS).

Other examples of ECMs are pericardium, stomach submucosa, liver basement membranes, urinary bladder submucosa, tissue mucosa, and dura mater. SIS is particularly useful, and can be made in the fashion described in U.S. Pat. No. 4,902,508 to Badylak et al.; U.S. Pat. No. 5,733,337 to Carr; 17 Nature Biotechnology 1083 (November 1999); and WIPO Publication WO 98/22158 of May 28, 1998, to Cook et al., which is the published application of PCT/US97/14855. All of these patents and publications are incorporated herein by reference.

Irrespective of the origin of the graft material 224 (synthetic versus naturally occurring), the graft material 224 can be made thicker by making multi-laminate constructs, for example SIS constructs as described in U.S. Pat. Nos. 5,968,096; 5,955,110; 5,885,619; and 5,711,969. All of these patents are incorporated herein by reference. In addition to xenogenic biomaterials, such as SIS, autologous tissue can be harvested as well for use in forming the graft material. Additionally, elastin or elastin-like polypeptides (ELPs) and the like offer potential as a material to fabricate the graft material.

In one preferred embodiment, the second tubular graft material 225 is a knitted mesh of bioabsorbable material. As used herein, the term "bioabsorbable" means a capacity to be taken in and made part of an existent whole, to be assimilated, or to be dissolved by an organism. For the purposes of this disclosure, "bioabsorbable" and "bioresorbable" have the same meaning, although for clarity only the term "bioabsorbable" is used. It is to be understood that wherever the term "bioabsorbable" is used, including the claims, the term "bioresorbable" can be substituted.

For example, the second tubular graft material 225 can be a VICRYL® (polyglactin 910) knitted surgical mesh. Such a knitted mesh of bioabsorbable material provides strength for temporary wound support, and is especially suitable for instances in which compliant and stretchable support material is desired.

In another preferred embodiment, the second tubular graft material 225 can be a woven mesh of bioabsorbable material. For example, the second tubular graft material 225 can be a VICRYL® (polyglactin 910) woven surgical mesh. Such a woven mesh provides a more occlusive graft than a knitted mesh.

VICRYL® knitted and woven meshes are each prepared from a synthetic absorbable copolymer of glycolide and lactide, derived respectively from glycolic and lactic acids. The meshes are prepared from uncoated, undyed fiber identical in composition to that used in VICRYL® synthetic absorbable suture. The absorption of VICRYL® mesh materials is minimal until about six weeks post implantation, and is essentially complete between between 60 and 90 days. This time period can be selectively varied by an appropriate substitution of materials.

Other bioabsorbable materials that can be suitably woven or knitted into a surgical mesh to form the second tubular graft material 225 are DEXON PLUS®), MAXON®), and PDS®). A DEXON PLUS®) absorbable mesh is prepared from a synthetic polyglycolic acid. A MAXON®) monofilament absorbable mesh is prepared from a polyglyconate. A PDS®) monofilament absorbable mesh is prepared from a polydioxanone. Other bioasborbable surgical materials that are known in the are can also be fabricated into a mesh to form the second tubular graft material 225.

Figure 4:
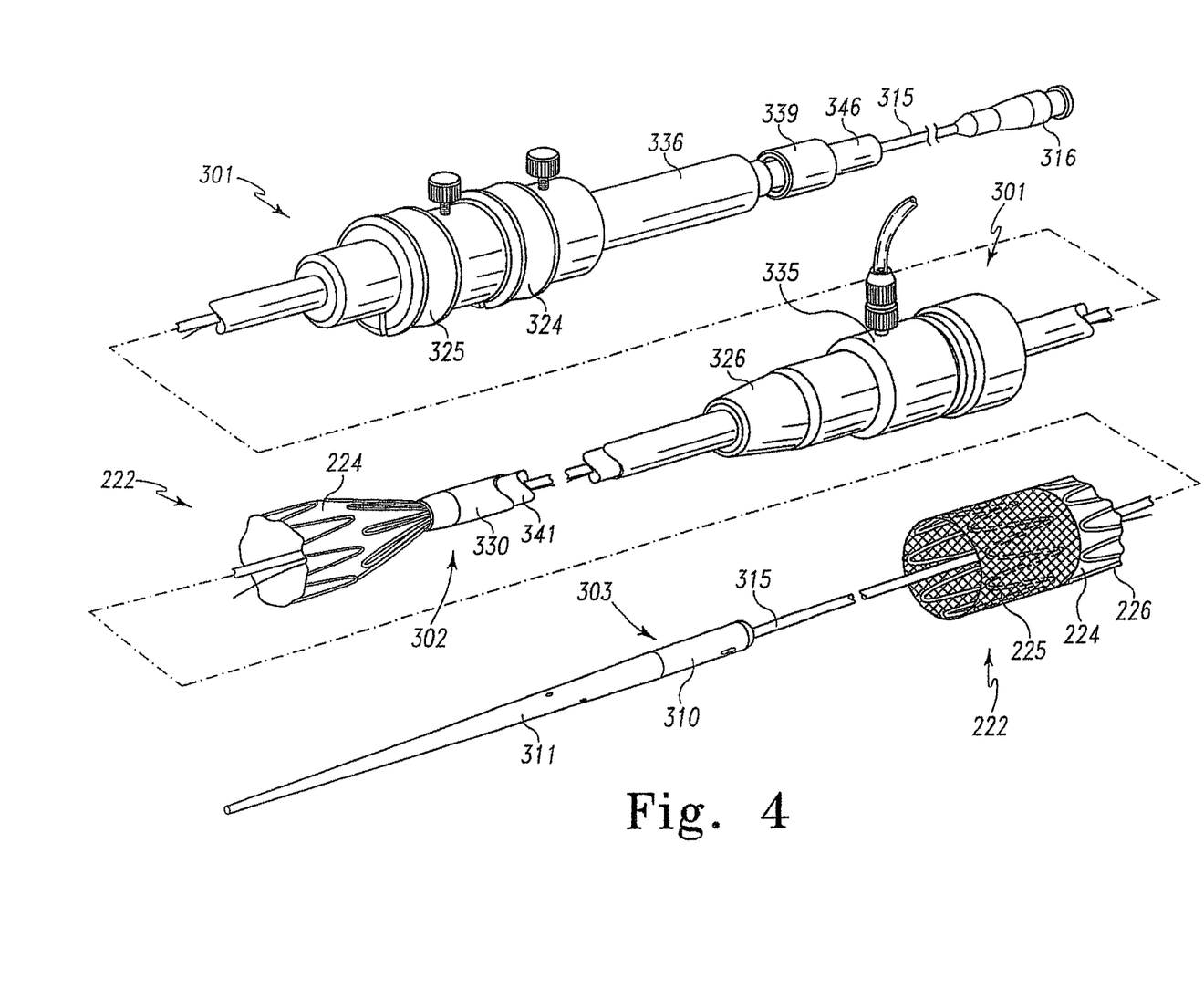
FIG. 4 is an exploded perspective view of an introducer view with the prosthesis of FIG. 3 partially deployed.

The self-expanding stents 226 cause the prosthesis 222 to expand following its disengagement from an introducer, shown in FIG. 4. When the prosthesis 222 is expanded in the aorta 102 (see FIG. 10), the proximal most self-expanding stents 226 pushes the second tubular graft material 225 against the flap 118, closing blood flow to the false lumen 110.

The prosthesis 222 shown in FIG. 3 can be deployed via any method known in the art, and preferably by the method described in PCT Patent Publication Number NO. WO98/53761. In this method, the prosthesis 222 can be inserted by an introducer via a surgical cut-down into a femoral artery. The prosthesis 222 can then advanced into the desired position over a stiff wire guide using endoluminal interventional techniques.

FIGS. 4-9 show an endovascular deployment system, also known as an introducer, for deploying the intraluminal prosthesis 222 in a lumen of a patient during a medical procedure. The introducer includes an external manipulation section 301, a distal positioning mechanism and attachment region 302 and a proximal positioning mechanism and attachment region 303.

Figure 5:
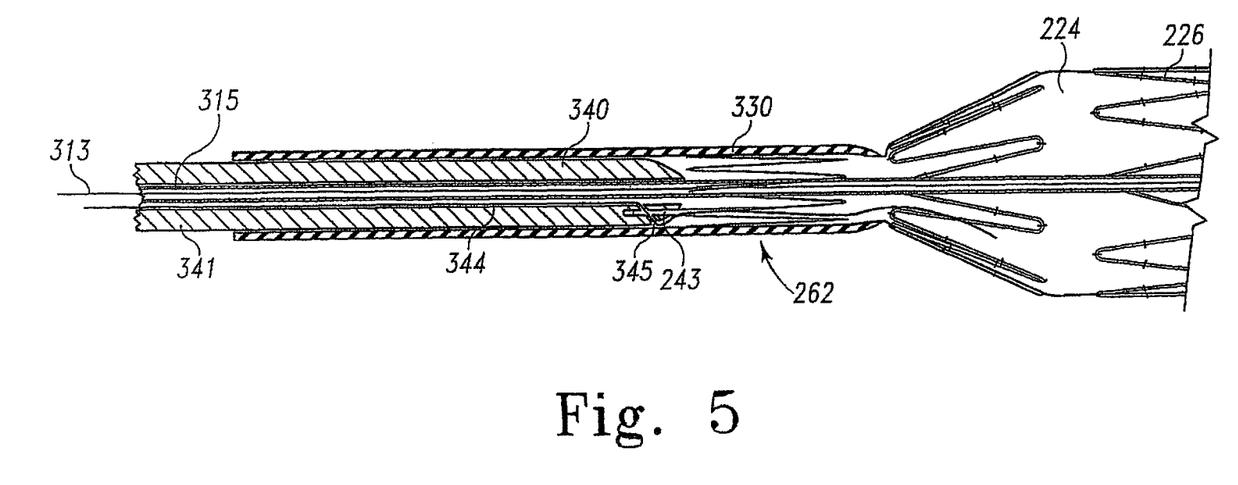
FIG. 5 is a sectional detail view of the portion of the introducer of FIG. 4 around the distal end of the prosthesis.
Figure 6:
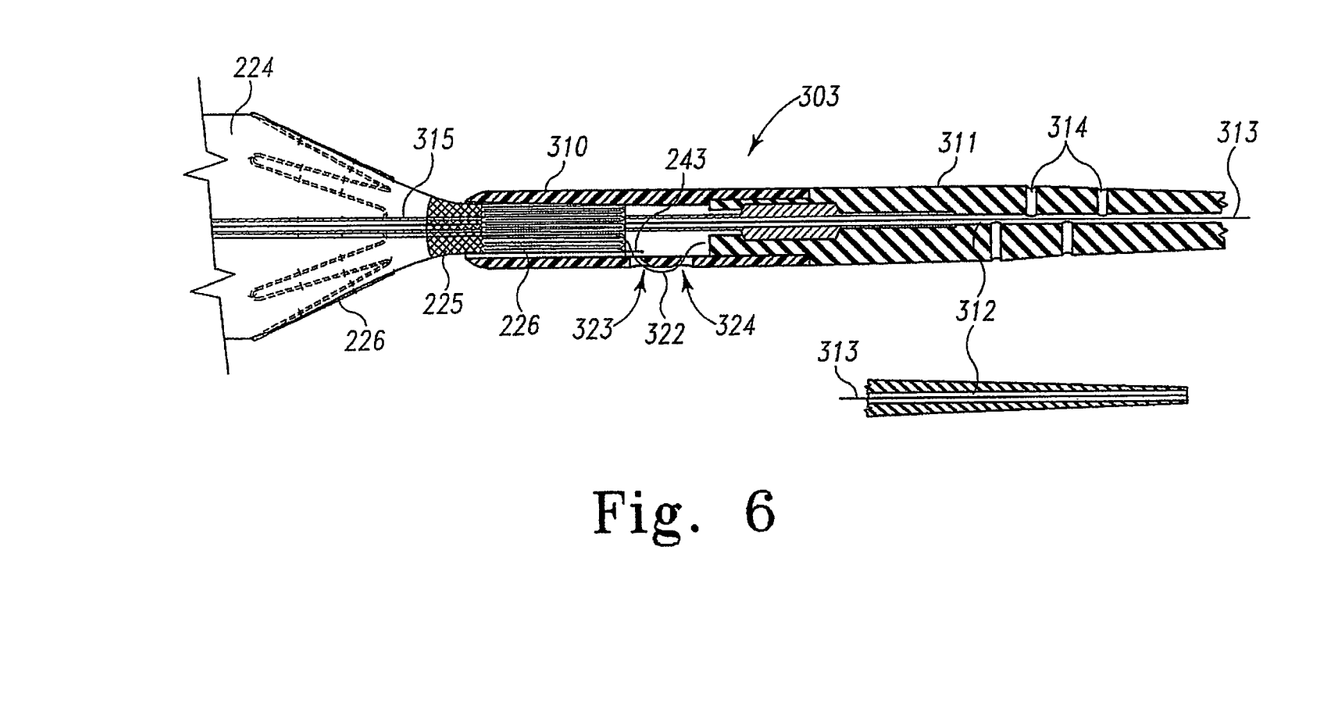
FIG. 6 is a sectional detail view of the portion of the introducer of FIG. 4 around the proximal end of the prosthesis.

First, a guide wire 313, shown in FIGS. 5 and 6, is introduced into the femoral artery and advanced until its tip is beyond the region into which the prosthesis 222 is to be deployed. During the medical procedure to deploy the prosthesis 222, the distal and proximal attachment regions 302 and 303 will travel over the guide wire 313 and through the lumen to a desired deployment site. The external manipulation section 301, which is acted upon by a user to manipulate the introducer, remains outside of the patent throughout the procedure.

FIGS. 5 and 6 illustrate distal and proximal retention and release mechanisms of the introducer. During the placement phase of the medical procedure, the prosthesis 222 is retained in a compressed condition by sheath 330. The sheath 330 extends distally to a gripping and haemostatic sealing means 335 of the external manipulation section 301, shown in FIGS. 4 and 7.

FIG. 6 shows the proximal attachment region 303 in greater detail. The proximal attachment region 303 includes a cylindrical sleeve 310. The cylindrical sleeve 310 has a long tapered flexible extension 311 extending proximally. The flexible extension 311 has an internal longitudinal aperture 312. The longitudinal aperture 312 facilitates advancement of the tapered flexible extension 311 along the insertion wire 313. The aperture 312 also provides a channel for the introduction of medical reagents, which will flow through openings 314. For example, it may be desirable to supply a contrast agent to allow angiography to be performed during placement and deployment phases of the medical procedure.

Figure 9:
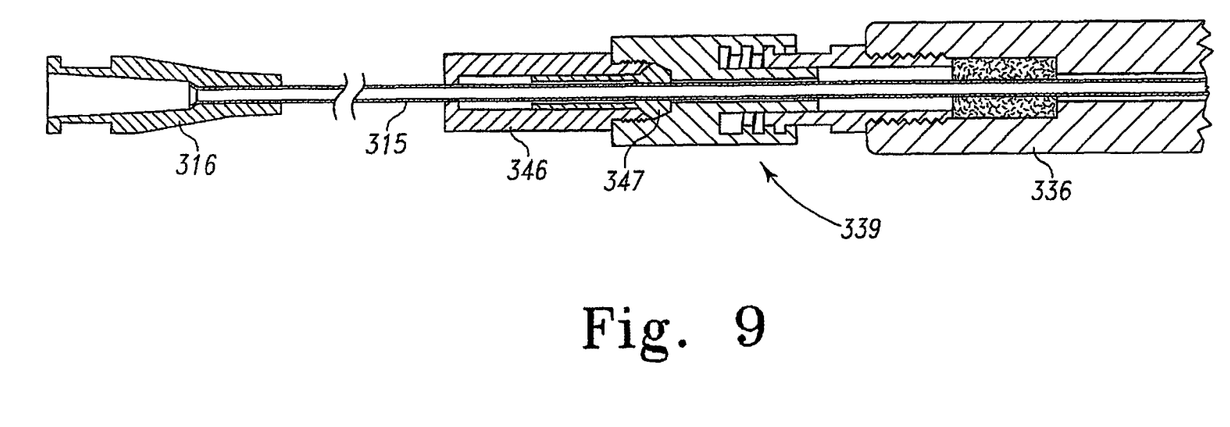
FIG. 9 is a sectional detail view of the portion of the introducer of FIG. 4 around the pin vise clamp and the medical reagent introduction tube.

A thin walled tube 315 is fastened to the extension 311. The thin-walled tube 315 is flexible so that the introducer can be advanced along a relatively tortuous vessel, such as a femoral artery, and also to allow manipulation longitudinally and rotationally of the proximal attachment region 303. The thin-walled tube 315 extends through the introducer to the manipulation section 301, terminating at a connection means 316, as shown in FIG. 9.

Figure 8:
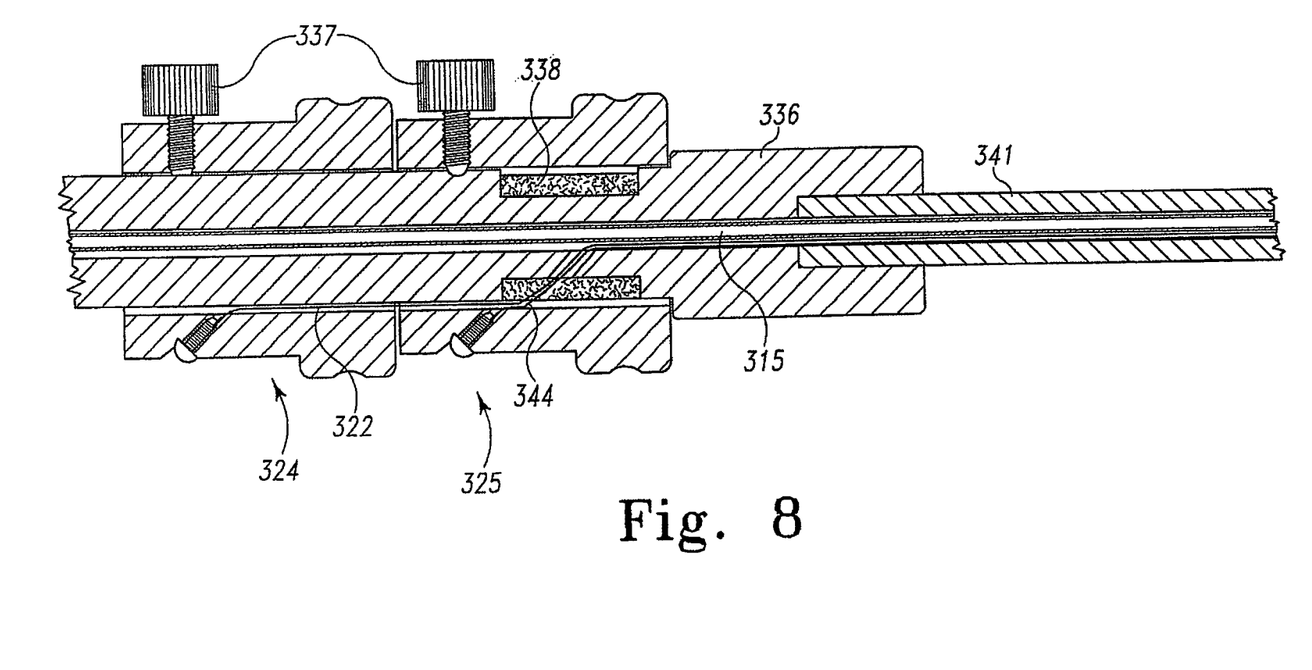
FIG. 8 is a sectional detail view of the portion of the introducer of FIG. 4 around the trigger wire release mechanisms.

As shown in FIG. 5, a tube 341 is coaxial with the radially outside the thin-walled tube 315. The tube 341 is "thick-walled", that is to say the thickness of its wall is several times that of the thin-walled tube 315. A sheath 330 is coaxial with and radially outside the thick-walled tube 341. The thick-walled tube 341 and the sheath 330 extend distally to the manipulation region 1, as shown in FIGS. 4 and 8.

During assembly of the introducer, the sheath 330 is advanced over the cylindrical sleeve 310 of the proximal attachment region 303 while the prosthesis 222 is held in a compressed stated by an external force. A distal attachment or retention section 340 is formed in the thick-walled tube 341 to retain the distal end of the prosthesis 222. Alternatively, the distal attachment section 340 can be a separate piece coupled to the thick-walled tube 341.

As shown in FIG. 6, the proximal-most self-expanding stent 226 has a retaining loop 243 which is held in place by a trigger wire 322, which is further threaded through a pair of apertures 323 and 324. The proximal-most stent 226 can be released by retracting the sheath 330, removing the trigger wire 322, and then sliding the proximal attachment region 303, including the retention device 310, proximally away from the stent 226.

Once the retention device 310 has cleared the proximal-most stent 226, the stent 226 will expand. The trigger wire 322 and the proximal wire release mechanism 324 form a control member to selectively release the retention device 310 from the prosthesis 222 by holding the self-expanding stent 226 in the retention device 310 until the prosthesis 222 is positioned at a desired site in the lumen.

As shown in FIG. 5, the distal end 262 of the prosthesis 222 is retained by the distal attachment section 340 of the thick-walled tube 341. The distal end 262 of the prosthesis 222 has a retention loop 243 through which a distal trigger wire 344 extends. The distal trigger wire 344 extends through an aperture 345 in the distal attachment section 340 into the annular region between the thin-walled tube 315 and the thick-walled tube 341.

As shown in FIG. 8, the distal trigger wire 344 extends through the annular space between the thick-walled plastic tube 341 and the thin-walled tube 315 to the manipulation region 301. The distal trigger wire 344 exits the annular space at a distal wire release mechanism 325. The distal trigger wire 344 and the distal wire release mechanism 325 form a control member to selectively disengage the distal retention section 340 from the prosthesis 222 when the prosthesis is positioned at a desired site in the lumen.

Figure 7:
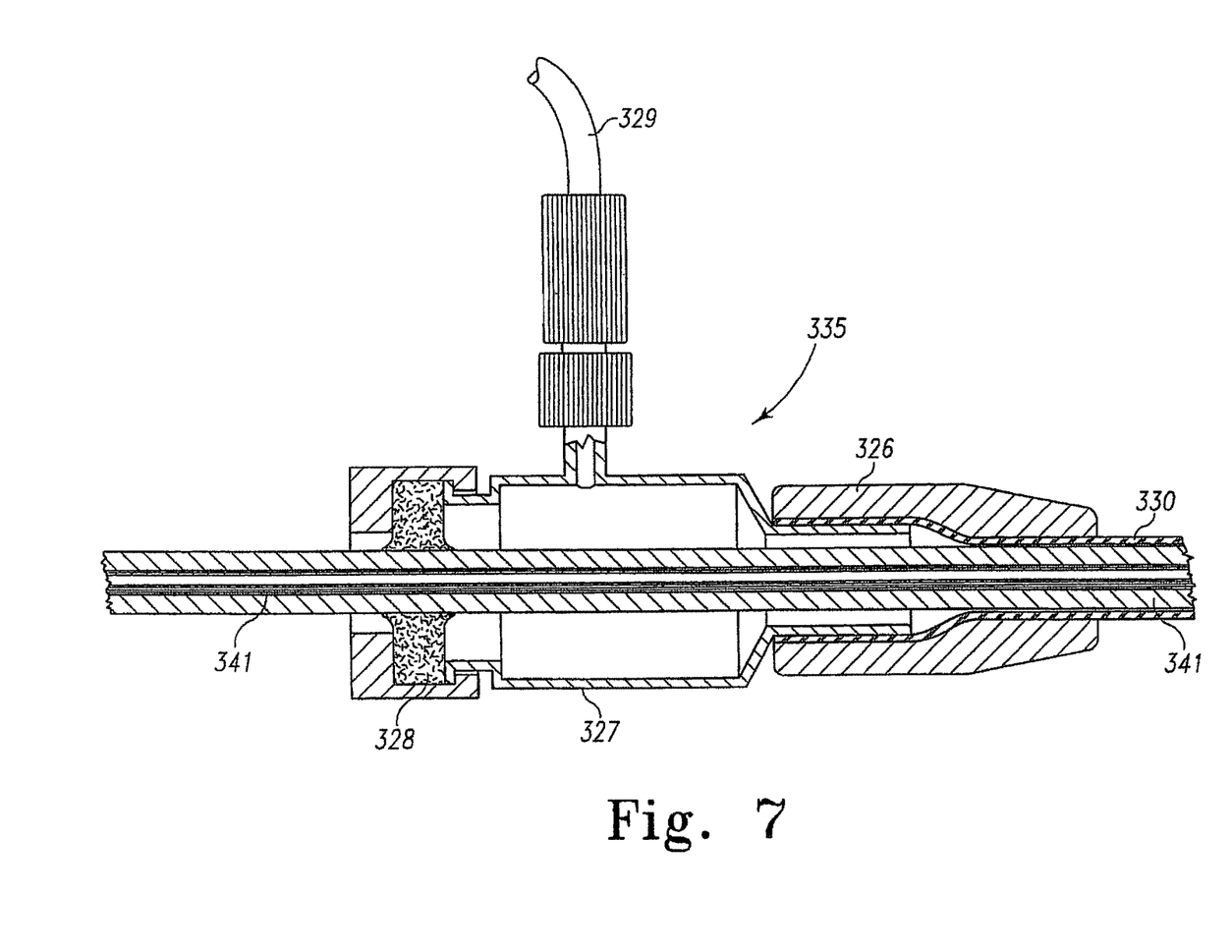
FIG. 7 is a sectional detail view of the portion of the introducer of FIG. 4 around the haemostatic seal.

FIG. 7 shows the haemostatic sealing means 335 of the external manipulation section 301 in greater detail. The haemostatic sealing means 335 includes a haemostatic seal 327 and a side tube 329. The haemostatic seal 327 includes a clamping collar 326 that clamps the sheath 330 to the haemostatic seal 327. The haemostatic seal 327 also includes a silicone seal ring 328. The silicone seal ring 328 forms a haemostatic seal around the thick-walled tube 341. The side tube 329 facilitates the introduction of medical reagents between the thick-walled tube 341 and the sheath 330.

FIG. 8 shows a proximal portion of the external manipulation section 301. The release wire actuation section has a body 336 that is mounted onto the thick-walled tube 341. The thin-walled tube 315 passes through the body 336. The distal wire release mechanism 325 is mounted for slidable movement on the body 336. Similarly, the proximal wire release mechanism 322 is mounted for slidable movement on the body 336. A pair of clamping screws 337 prevents inadvertent early release of the prosthesis 222.

The positioning of the proximal and distal wire release mechanisms 324 and 325 is such that the proximal wire release mechanism 324 must be moved before the distal wire release mechanism 325 can be moved. Therefore, the distal end 262 of the prosthesis 222 cannot be released until the proximal most self-expanding zigzag stent 226 has been released and anchored to the lumen. A haemostatic seal 338 is provided so that the release wires 322 and 344 can extend out through the body 336 to the release mechanisms 324 and 325 with unnecessary blood loss during the medical procedure.

FIG. 9 shows a distal portion of the external manipulation section 301. A pin vise 339 is mounted onto the distal end of the body 336. The pin vise 339 has a screw cap 346. When screwed in, the vise jaws 347 clamp against and engage the thin-walled tube 315. When the vise jaws 347 are engaged, the thin-walled tube 315 can only move with the body 336, and hence the thin-walled tube 315 can only move with the thick-walled tubed 341. With the screw cap 346 tightened, the entire assembly, except for the external sleeve 330, can be moved as one.

Regarding the introduction of reagents, FIG. 9 shows that the connection means 316 is adapted to accept a syringe to facilitate the introduction of reagents into the tube 315. The tube 315 is in fluid communication with the aperture 312 of the flexible extension 311. Therefore, reagents introduced into connection means 316 can flow through the aperture 312 and emanate from the openings 315 shown in FIG. 6 and discussed above.

Figure 10:
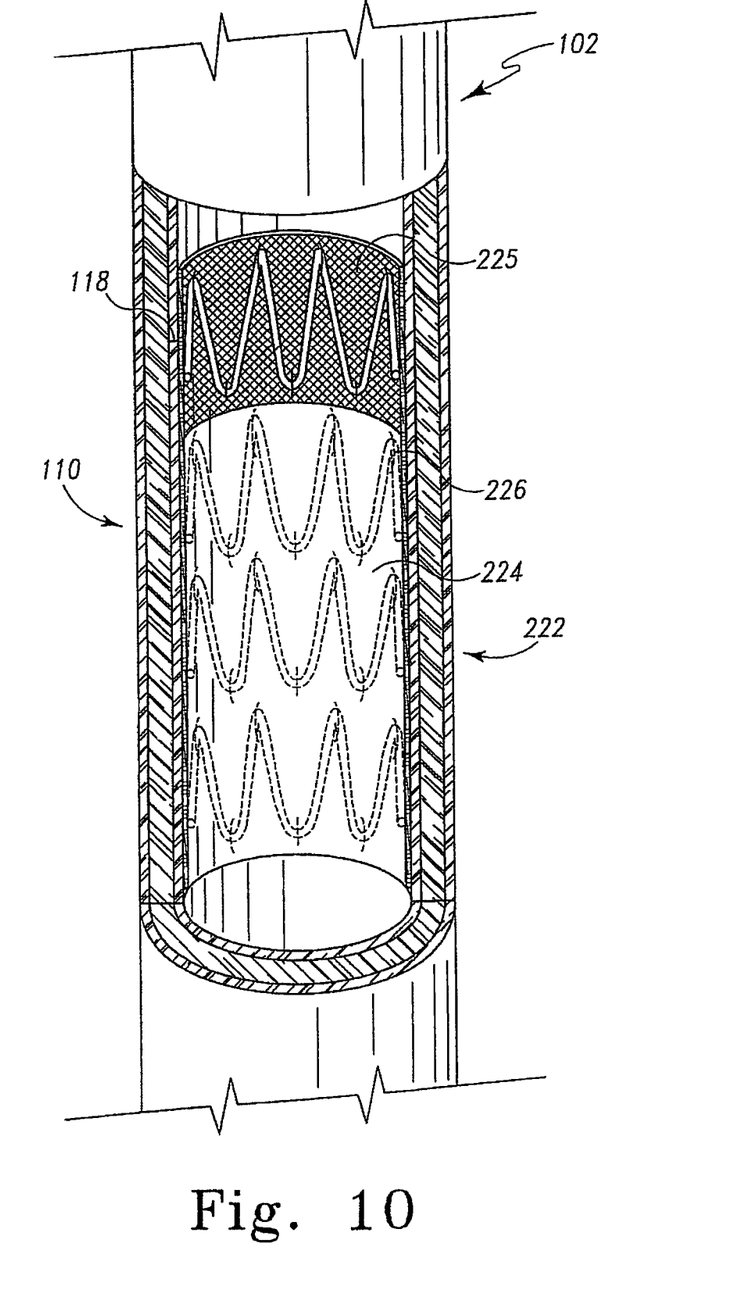
FIG. 10 is a partial cut-away view of the aorta of FIGS. 1 and 2 with the endoluminal prosthesis of FIG. 3 situated in the aorta.

FIG. 10 is a cut-away view of the aorta 102 showing the prosthesis 222 placed in a position to occlude the false lumen 110 and seal the intimal flap 118. The bioabsorbable graft material 225 holds the flap 118 in place so that the flap 118 may reattached to the media 106 of the aorta 102, and heal. Within a few weeks to several months of a procedure implanting the prosthesis 222, the second tubular graft material 225 should be absorbed, and the intimal flap 118 may be healed. The first tubular graft material 224 and the associated stents 226 will continue hold closed a false lumen 110 in the media 106 below the flap 118, so that the media 106 may also heal.

Throughout this specification, unless the context requires otherwise, the words "comprise" and "include" and variations such as "comprising" and "including" will be understood to imply the inclusion of an item or group of items, but not the exclusion of any other item or group items.

While various embodiments of the invention have been described, it will be apparent to those of ordinary skill in the art that many more embodiments and implementations are possible within the scope of the invention. Furthermore, although various indications have been given as to the scope of this invention, the invention is not limited to any one of these but can reside in two or more of these combined together. Accordingly, the invention is not to be restricted except in light of the attached claims and their equivalents.

What is claimed is:

1. An endoluminal prosthesis comprising:
a tube having a first portion comprising a first tubular graft material being non-porous and non-bioabsorbable and a second portion comprising a second tubular graft material, said second portion being entirely bioresorbable such that no part of the second portion remains in situ after a period of time from a few weeks to several months thereby providing temporary wound support, wherein the first and second portions are arranged coaxially in series and coupled to one another; and an expandable stent coupled to the tube at the second portion, wherein after bioresorption of the second tubular graft material only the expandable stent remains.

2. The endoluminal prosthesis of claim 1, wherein second tubular graft material comprises:
a copolymer of glycolide and lactide;
polyglactin;
polyglycolic acid;
polyglyconate; or
polydioxanone.

3. The endoluminal prosthesis of claim 1, further comprising a plurality of self-expanding stent elements that are coupled along a length of the first portion of the tube.

4. The endoluminal prosthesis of claim 1, wherein the stent comprises a plurality of self-expanding stent elements that are coupled along a length of the second portion of the tube.

5. The endoluminal prosthesis of claim 1, wherein the expandable stent is a self-expanding stent.

6. The endoluminal prosthesis of claim 1, wherein the second tubular graft material is porous.

7. The endoluminal prosthesis of claim 1, wherein the non-porous material comprises a derived collagen material.

8. The endoluminal prosthesis of claim 7, wherein the derived collagen material is an extracellular matrix.

9. The endoluminal prosthesis of claim 8, wherein the extracellular matrix is:
small intestinal submucosa;
stomach submucosa;
pericardium;
liver basement membrane; or
urinary bladder submucosa.

10. The endoluminal prosthesis of claim 1, wherein the first portion of the tube comprises a synthetic material.

11. The endoluminal prosthesis of claim 10, wherein the synthetic material is a polyester, polytetrafluoroethylene, or expanded polytetrafluoroethylene.

12. The endoluminal prosthesis of claim 1, wherein the prosthesis is compressible for endoluminal placement in an aorta.

13. An endoluminal prosthesis comprising:
a tube having a first portion comprising a first tubular graft material being non-porous and non-bioabsorbable and a second portion comprising a second tubular graft material, said second portion being entirely bioresorbable such that no part of the second portion remains in situ after a period of time from a few weeks to several months thereby providing temporary wound support, wherein the first and second portions are arranged coaxially in series and coupled to one another, wherein second tubular graft material comprises at least one of polyglactin, polyglycolic acid, polyglyconate, polydioxanone and a copolymer of a glycolide and lactide; and
an expandable stent coupled to the tube at the second portion, wherein after bioresorption of the second tubular graft material only the expandable stent remains.

14. The endoluminal prosthesis of claim 13, wherein the stent comprises a plurality of self-expanding stent elements that are coupled along a length of the first portion of the tube.

15. The endoluminal prosthesis of claim 14, including a plurality of self-expanding stent elements that are coupled along a length of the second portion of the tube.

16. The endoluminal prosthesis of claim 13, wherein the second tubular graft material is porous.

17. An endoluminal prosthesis comprising:
a tube having a first portion comprising a first tubular graft material being non-porous and non-bioabsorbable and a second portion comprising a second tubular graft material, said second portion being entirely bioresorbable such that no part of the second portion remains in situ after a period of time from a few weeks to several months thereby providing temporary wound support, wherein the first and second portions are arranged coaxially in series and coupled to one another, wherein second tubular graft material is porous and comprises at least one of polyglactin, polyglycolic acid, polyglyconate, polydioxanone and a copolymer of a glycolide and lactide;
an expandable stent coupled to the tube, wherein the stent comprises a plurality of self-expanding stent elements that are coupled along a length of the first portion of the tube;
a second stent coupled to the second portion of the tube, wherein the second stent comprises a plurality of self-expanding stent elements that are coupled along a length of the second portion of the tube, wherein after bioresorption of the second tubular graft material only the plurality of self-expanding stents remain at the second portion of the tube;
wherein the non-porous material comprises a derived collagen material, wherein the derived collagen material is an extracellular matrix, and
wherein the extracellular matrix is small intestinal submucosa, stomach submucosa, pericardium, liver basement membrane, or urinary bladder submucosa.

* * * * *